United States Patent
Wolfe et al.

(10) Patent No.: US 8,818,755 B2
(45) Date of Patent: Aug. 26, 2014

(54) CONTAINER THICKNESS MEASURING SYSTEMS AND METHODS

(75) Inventors: Georg V. Wolfe, Butler, PA (US); William E. Schmidt, Gibsonia, PA (US); Jeffery A. Peterson, Pittsburgh, PA (US); Edward J. Fisher, Butler, PA (US)

(73) Assignee: AGR International, Inc., Butler, PA (US)

( * ) Notice: Subject to any disclaimer, the term of this patent is extended or adjusted under 35 U.S.C. 154(b) by 115 days.

(21) Appl. No.: 13/878,622

(22) PCT Filed: Oct. 12, 2011

(86) PCT No.: PCT/US2011/055990
§ 371 (c)(1),
(2), (4) Date: Jun. 5, 2013

(87) PCT Pub. No.: WO2012/051321
PCT Pub. Date: Apr. 19, 2012

(65) Prior Publication Data
US 2013/0268237 A1    Oct. 10, 2013

Related U.S. Application Data

(60) Provisional application No. 61/392,278, filed on Oct. 12, 2010.

(51) Int. Cl.
*G01B 5/02* (2006.01)
*G01B 11/06* (2006.01)
*G01N 21/90* (2006.01)

(52) U.S. Cl.
CPC ............... *G01B 11/06* (2013.01); *G01N 21/90* (2013.01)
USPC ........... 702/172; 702/189; 356/630; 356/631; 356/632

(58) Field of Classification Search
USPC ........... 702/172, 189; 356/630–632; 144/399, 144/410; 72/9.2, 9.4, 11.8, 16.9, 18.8
See application file for complete search history.

(56) References Cited

U.S. PATENT DOCUMENTS

| | | | |
|---|---|---|---|
| 4,991,964 A | 2/1991 | Forgey et al. | |
| 6,172,748 B1 * | 1/2001 | Sones et al. | 356/237.1 |
| 6,788,984 B2 * | 9/2004 | Plotkin | 700/97 |
| 6,806,459 B1 * | 10/2004 | Ringlien et al. | 250/223 B |
| 7,414,740 B2 * | 8/2008 | Wilke et al. | 356/632 |
| 7,711,182 B2 | 5/2010 | Beardsley | |
| 2002/0146172 A1 * | 10/2002 | Nair et al. | 382/195 |
| 2005/0046874 A1 * | 3/2005 | Caton et al. | 356/630 |

FOREIGN PATENT DOCUMENTS

GB       2221533 A    2/1990

* cited by examiner

*Primary Examiner* — Elias Desta
(74) *Attorney, Agent, or Firm* — K&L Gates LLP

(57) ABSTRACT

Various embodiments are directed to systems and methods for measuring a thickness of a container. For example, a control device may receive data indicating a surface topology of the container and based on the surface topology of the container, instruct a multi-axis positioning system to position a sensor relative to a first point of the container such that: a distance from the sensor to a surface at the first point is about equal to a predetermined distance; and the sensor direction is about normal to the surface at the first point. Data indicating the thickness at the first point may be received from the sensor.

21 Claims, 14 Drawing Sheets

CONTAINER THICKNESS MEASURING SYSTEMS AND METHODS

PRIORITY CLAIM

This application claims the benefit of U.S. Provisional Patent Application Ser. No. 61/392,278 filed on Oct. 12, 2010, which is incorporated herein by reference in its entirety.

BACKGROUND

Test methods and devices exist within the glass and plastic container industry for measuring wall thickness and other properties of glass and plastic containers during and after formation. One class of devices, capacitive sensing devices, are used to measure the wall thickness of glass containers using one or more on-line capacitive strip sensors or heads. After being formed and annealed, glass containers are rolled across the strip sensors. The devices utilize readings from the strip sensors to determine an indication of the amount of material present and, therefore, the thickness of the container. An example of such a capacitive thickness measuring device is the On-Line Thickness (OLT) machine manufactured by AGR International of Butler, Pa. Other similar machines are available from several manufacturers throughout the world.

Another class of devices measures the thickness of glass and plastic containers using non-contact reflective and/or absorptive techniques. These devices are typically positioned in a rotating inspection machine downstream from the forming machinery. The rotating inspection machine may contain several inspection pockets for performing a variety of inspection tasks in addition to the non-contact reflective thickness measurement. The rotating inspection machine sequentially indexes containers through each inspection pocket. Once in the pocket, each container is mechanically stopped and rotated. As a container is stopped and rotated in the inspection pocket, sensors and emitters are deployed and used to direct radiation towards the container. Mathematical techniques are used to derive container thickness, based on the radiation either reflected or absorbed.

Existing capacitive and optical techniques are limited in accuracy and the quantity of information that they are able to provide. Accordingly, they are also limited in their ability to provide information that is useful to control the container-making process.

FIGURES

Various embodiments of the present invention are described here by way of example in conjunction with the following figures, wherein.

DESCRIPTION

Various embodiments are directed to systems and methods for measuring containers utilizing non-contact optical techniques. Various container properties may be measured including, for example, wall thickness, coating thickness, surface topology, etc. It will be appreciated that, with many non-contact optical techniques, the quality of obtained results may depend upon the positioning of the optical sensor. For example, chromatic optical techniques may provide superior results when the sensor is pointed in a direction about normal to the container surface. Other non-contact techniques may have different optimal angles relative to the container surface. Also, many non-contact optical techniques provide superior results when the sensor is maintained at a predetermined distance from the container surface. The predetermined distance may depend, for example, on the configuration of the sensor.

According to various embodiments, the systems and methods described herein may comprise and/or utilize a multi-axis sensor positioning device to position the optical non-contact sensor relative to the container surface. The sensor positioning device may be mechanically coupled to the sensor and may provide three degrees of movement. According to various embodiments, the three degrees of movement may comprise translation along a first direction axis, rotation about a second directional axis and rotation about a third directional axis. In some embodiments, additional movement of the container relative to the sensor may be provided by a container stage. In use, the sensor positioning device may position the sensor at a desired angle and distance from one or more points of the container surface. Measurements of the surface at the selected points may be taken while the sensor is appropriately positioned. The measurements may be used, for example, to develop mappings of container properties over the surface.

Figure 1:
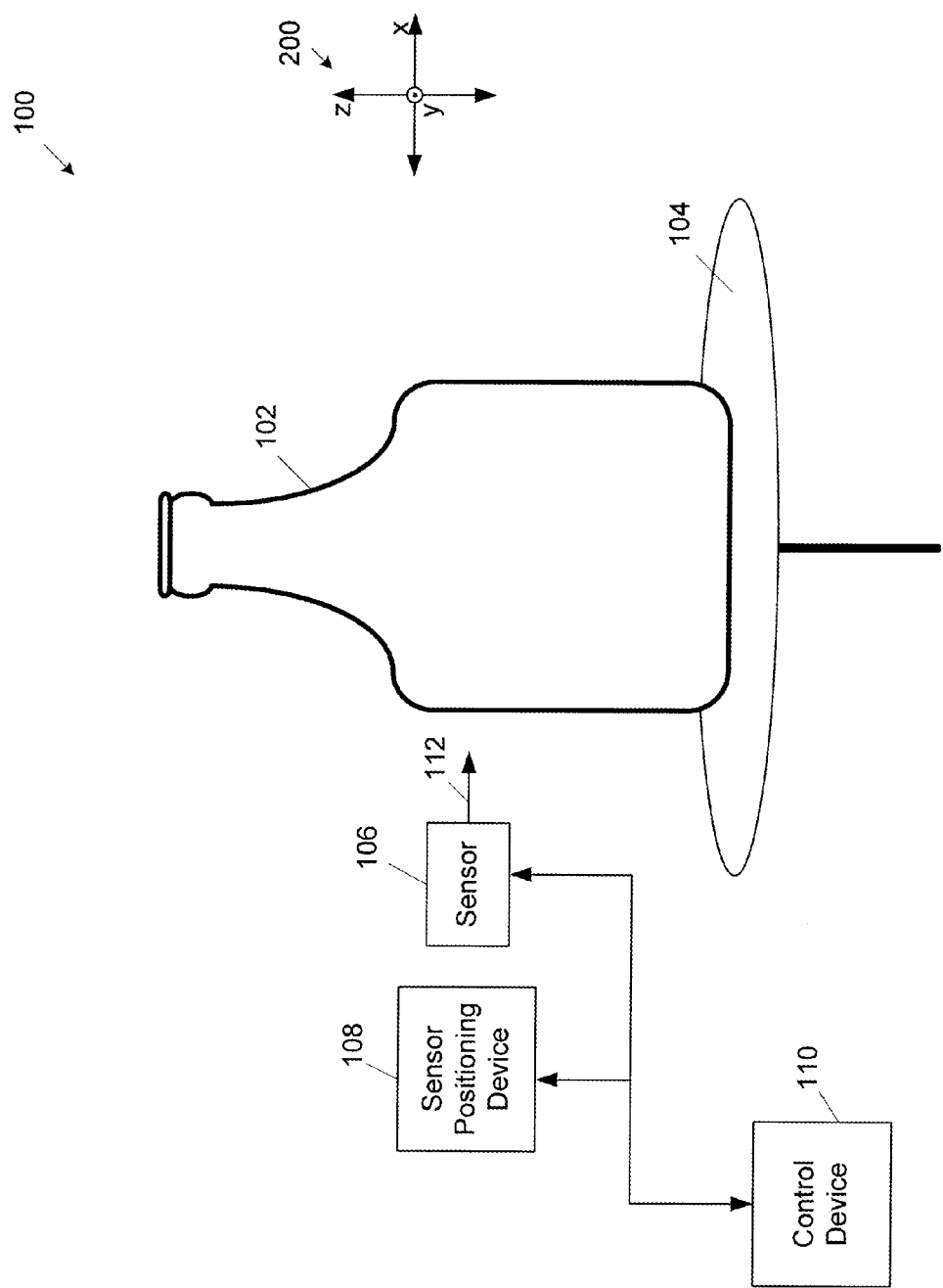
FIG. 1 illustrates one embodiment of a container measurement system for utilizing optical non-contact techniques to measure a container.

FIG. 1 illustrates one embodiment of a container measurement system 100 for utilizing optical non-contact techniques to measure a container 102. The system 100 may comprise a stage 104 for receiving and for supporting the container 102, as well as an optical sensor 106, the sensor positioning device 108, and a control device 110. The container 102 is illustrated in different forms in the various figures herein. It will be appreciated that the container 102 may represent any container suitable for measurement with the system 100. For example, the container 102 may be a glass or plastic bottle or other container. The control device 110 may be any suitable form of processor-based device or system, such as a computer, configured to control the motion of the sensor positioning device 108. In some embodiments, the control device 110 may include multiple functional modules. For example, the control device may comprise a functional module dedicated to the operation of the sensor 102 and an additional functional module or modules directed to other activities of the system 100 (e.g., operation of the sensor positioning device 108). In various embodiments, the control device 110 may also be in communication with the sensor 106 and may process signals received from the sensor 106 to derive measurements of the container 102. The system 100 may be implemented in any suitable instrument context. For example, the system 100 may be implemented in a piece of laboratory equipment, an on-line machine, an off-line sampling machine, etc. According to various embodiments, the container 102 may be placed on the stage 102 manually or utilizing any suitable type of ware handling device.

The sensor 106 may generally be directed towards the container in a sensor direction 112. The sensor 106 may comprise a single sensor or an array of sensors, and may be configured for any suitable type of optical non-contact measurement. For example, the sensor 106 may be configured to measure the distance and/or thickness of a wall of the container 102 (or a coating thereof) utilizing a chromatic method. According to a chromatic method, broadband illumination may be directed towards a surface of the container, for example, in the sensor direction. The broadband illumination may be focused by illumination optics of the sensor 106 exhibiting a high degree of chromatic aberration. For example, different wavelengths of the broadband illumination may be focused spatially at different distances from the sensor 106 along the sensor direction 112. Chromatically separated illumination may be reflected off of interfaces between different types of material back towards the sensor 106. For example, illumination may be reflected off of front and rear surfaces of a wall of the container 102. When the wall of the container comprises a coating, film or other covering, the illumination may also reflect off of the interfaces between these and other components of the container 102. Because different chromatic components of the illumination are focused at different distances from the sensor 106, the wavelength content of the illumination reflected at any given interface may indicate the distance of the interface from the sensor 106. The control device 110 may receive data indicating reflected illumination captured at the sensor 106. The control device 110 may be programmed to calculate distances from the sensor 106 to the different material interfaces based on this data. From these distances, the control device 110 may derive the distance between the sensor 106 and the surface of the container 102, the thickness of a wall of the container 102, the thickness of a coating on the container 102, etc. According to various embodiments, the sensor 106 may be in communication with the control device 110 according to any suitable wired or wireless communication method including, for example, USB, I2C, RS-232, etc. Examples of sensors and controllers for performing chromatic non-contact optical measurements are available, for example, from the PRECITEC GROUP of Gaggenau, Germany and VMA -Gesellschaft für visuelle Messtechnik and Automatisierung mbH of Wumbach, Germany.

It will be appreciated that, in various embodiments, the sensor 106 may be configured to operate according to other optical non-contact measurement techniques in addition to or instead of the chromatic techniques described above. For example, the sensor 106 may be configured to direct an illumination beam (e.g., a laser) towards the surface of the container 102 at an angle (e.g., a 45° angle) relative to a surface of the container. A portion of the illumination beam may reflect off of a front surface of the container wall, while a second portion may reflect off of a rear surface of the container wall. The sensor 106 may receive both the first and second portions of the reflected illumination beam. The spatial distance between the first and second portions may indicate a thickness of the wall of the container. For example, the control device 110 may receive from the sensor 106 an indication of the distance between the first and second illumination beam portions. Considering this distance and the refraction index of the container 102, the control device 110 may derive the container wall thickness. The sensor 106 may comprise a single illumination source and receiver configured to perform a single spot measurement or may be configured to comprise multiple illumination sources and receivers to take multiple measurements. Examples of sensors and controllers for performing measurements of this type may be available from VMA-Gesellschaft für visuelle Messtechnik and Automatisierung mbH of Wumbach, Germany. Any other optical thickness or other property measurement method may be implemented using the sensor 106. Another example thickness measurement method is disclosed by U.S. Pat. No. 6,549,292 to Schmidt, et al., entitled "Method and Apparatus for Inspecting Hollow Transparent Articles," which is incorporated herein by reference in its entirety.

Figure 2:
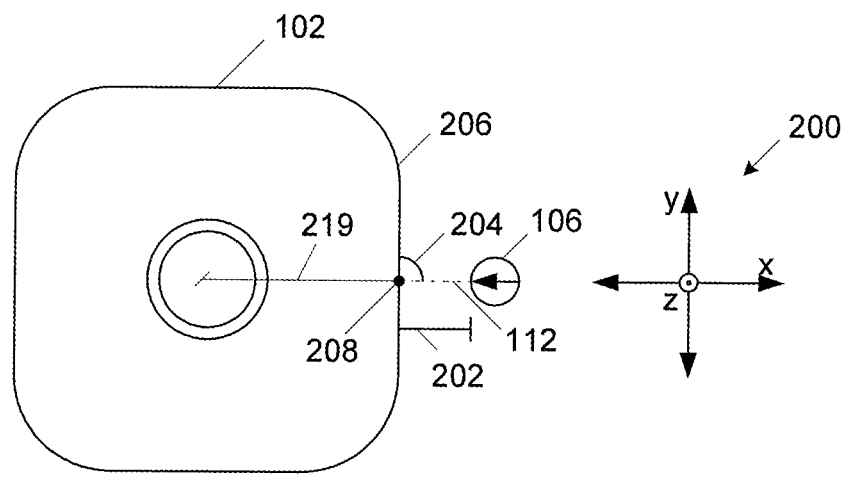
FIG. 2 illustrates a top view of the container of FIG. 1 showing one embodiment of the sensor directed to a point on a sidewall of the container.

The sensor positioning device 108 may be configured to maintain the sensor 106 such that the sensor direction 112 is about normal (e.g., perpendicular) to a surface of the container 102 and such that a normal distance from the sensor 106 to the container 102 is about constant. According to various embodiments, the sensor positioning device 108 may accomplish this by providing three degrees of motion. FIGS. 2-5 illustrate sensor positions that may be achievable with a sensor positioning device 108 having three degrees of motion, according to various embodiments. For example, FIG. 2 illustrates a top view of the container 102 showing one embodiment of the sensor directed to a point 208 on a sidewall 206 of the container 102. For reference, axis-indicator 200 shows three directional axes labeled x, y and z.

The point 208 may be located at a relatively flat sidewall 206 of the container 102. The direction of the sensor 106 (indicated by direction 112) may be normal or perpendicular to the point 208. Accordingly, the angle 204 between the sensor direction 112 and the tangent of the point 208 may be equal to 90°. According to various embodiments, the angle 204 may deviate from 90° by a predetermined tolerance, which may be set to any suitable value based on the tolerances of the sensor 106. For example, in some embodiments, the angle 204 may be equal to 90°±7.5°. In other embodiments, the tolerance may be equal to 90°±15°. Further, the sensor 106 may be separated from the point 208 by a distance 202 in the x-y plane. If there is no curvature of the container 102 at point 208 in the x-y plane, then the distance 202 may be the normal distance from the sensor 106 to the point 208. If there is curvature of the container 102 at the point 208, then the normal distance from the sensor 106 to the point 208 may be determined based on the distance 202 in the x-z plane as well as a second distance in the x-z plane. The normal distance may be determined according to any suitable factor or factors including, for instance, properties of the sensor 106. For example, when the sensor 106 is configured according to chromatic optical methods, the normal distance may be determined based on the spectral spread of the illumination by the sensor optics. For example, in various embodiments, the normal distance may be 1 inch.

Figure 3:
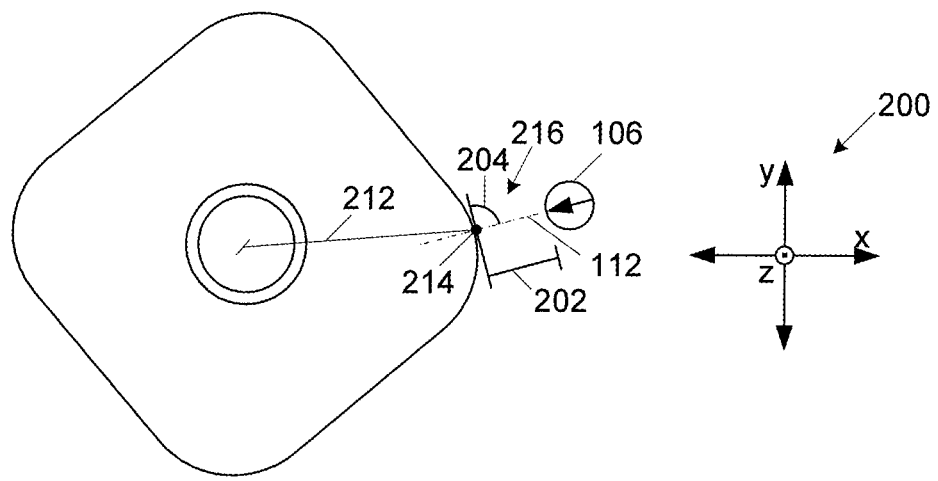
FIG. 3 illustrates a top view of the container of FIG. 1 showing one embodiment of the sensor directed to a point on a curved sidewall portion of the container.

FIG. 3 illustrates a top view of the container 102 showing one embodiment of the sensor 106 directed to a point 214 on a curved sidewall portion 216 of the container 102. The sidewall portion 216, as illustrated, is curved in the x-y plane. Relative to FIG. 2, the container 102, as shown in FIG. 3, has been rotated about the direction of the z-axis. (Alternatively, the sensor 106 may have been rotated about the container 102.) A diameter 212 of the container 102 at the point 214 may be greater than a diameter 210 of the container 102 at the point 208 shown in FIG. 2. Accordingly, in order to keep the normal distance from the sensor 106 to the point 214 substantially constant, the sensor positioning device 108 (not shown in FIG. 3) may translate the sensor 106 along the direction of the x-axis. Similarly, because the point 214 is on a curved portion 216 of the container 102, the sensor positioning device 108 may rotate the sensor 106 about the direction of the z-axis as well to keep the angle 204 within the tolerance described above.

Figure 4:
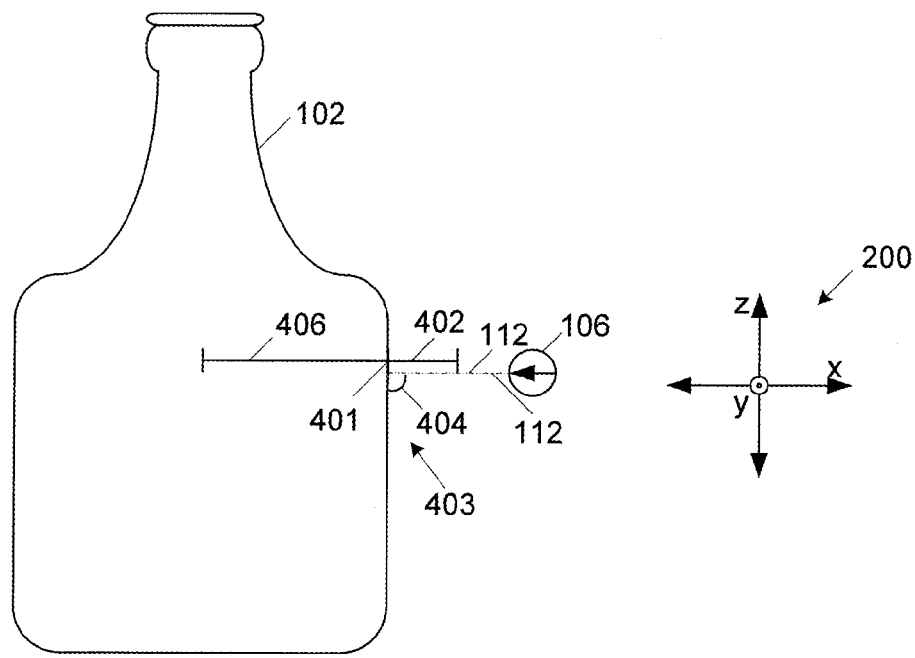
FIG. 4 illustrates a side view of the container of FIG. 1 showing one embodiment of the sensor directed to a point on a sidewall portion of the container.
Figure 5:
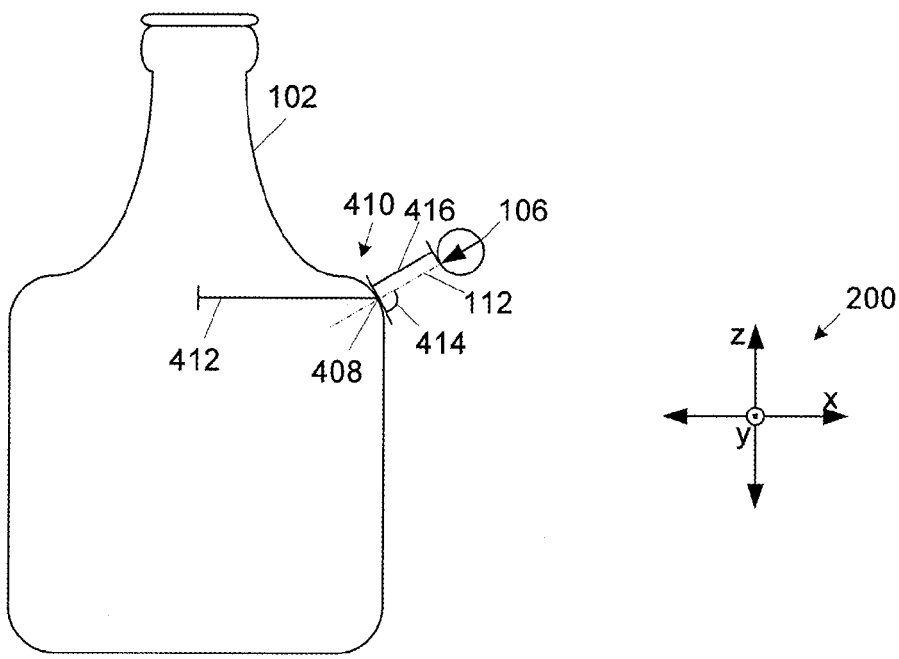
FIG. 5 illustrates a side view of the container of FIG. 1 showing one embodiment of the sensor directed to a point on a curved sidewall portion of the container.

FIG. 4 illustrates a side view of the container 102 showing one embodiment of the sensor 106 directed to a point 401 on the sidewall portion 403 of the container 102. The point 401 may be the same as the point 208 or the point 214. As illustrated, the sensor 106 is positioned a distance 402 from the container 102 and the direction of the sensor 106 relative to the point 401 (angle 404) may be about normal (e.g., within acceptable tolerances, as described above). FIG. 5 illustrates a side view of the container 102 showing one embodiment of the sensor 106 directed to a point 408 on a sidewall portion 410 of the container 102. The sidewall portion 410, as illustrated, is curved in the x-z plane. Relative to FIG. 4, the sensor 106 is translated along the direction of the z-axis. This may be brought about by actually translating the sensor 106 or by translating the container 102. The angle 414 of the sensor direction 112 relative to the point 408 may be about 90° (e.g., the direction 112 may be normal to the point 408). Also the normal distance between the sensor 106 and the point 408 may be maintained at the predetermined constant. The illustrated distance 416 may either be, or be a component of, the normal distance. It can be seen that moving the sensor 106 from the position shown in FIG. 4 to the position shown in FIG. 5 may involve rotation about the direction of the y-axis, due to the difference in curvature of the points 401, 408 in the x-z plane. In addition, translation in the direction of the x-axis may occur to maintain the normal distance at the predetermined level.

Figure 6:
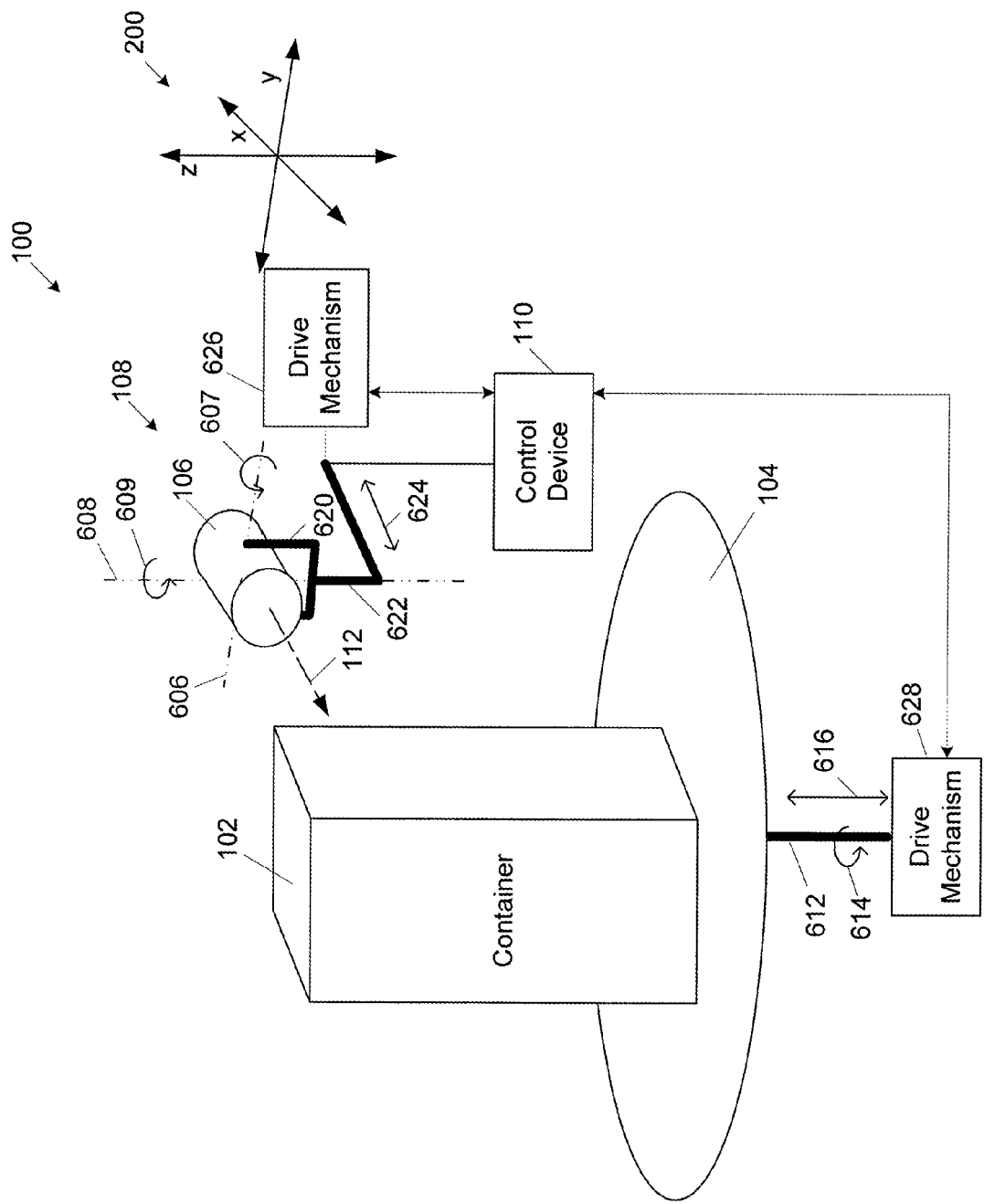
FIG. 6 illustrates one embodiment of the container measurement system of FIG. 1 showing additional details of the sensor positioning device and stage.

FIG. 6 illustrates one embodiment of the container measurement system 100 showing additional details of the sensor positioning device 108 and stage 104. For example, the sensor positioning system 108, as shown in FIG. 6, may be configured to move the sensor 106 in the manner shown in FIGS. 2-5 above. The direction of the sensor 106 may be indicated by 112. The sensor 106 may be mounted on a first yoke member 620. The yoke member 620 may be coupled to the sensor 106 in a manner allowing the sensor 106 to rotate about the direction of the z-axis direction, indicated by axis 606 and arrow 607. For example, the first yoke member 620 may comprise a bracket or other mechanical device for receiving the sensor 106. The first yoke member 620 may be coupled to a second member 622. The second member 622 may be rotatable, causing rotation of the sensor 106 about the z-axis direction, indicated by axis 608 and arrow 609. In addition, the second member 622 may be translatable in the direction of the x-axis, indicated by arrow 624. In this way, the sensor positioning device 108 may allow the sensor 106 to be translatable in the direction of the x-axis and rotatable about the direction of the y-axis and the direction of the z-axis.

Translation and rotation of the sensor positioning device 108 and sensor 106 may be powered by a drive mechanism 626. The drive mechanism 626 may comprise one or more individual motors or other drive devices coupled to the sensor positioning device 108 and under the control of the control device 110. For example, the drive device or devices may comprise one or more stepper motors, voice coil motors, hydraulic cylinders, pneumatic cylinders, etc. In some embodiments, the drive mechanism 626 may be directly coupled to the sensor positioning device 108, or may be coupled to the device 108 via one or more transmission components (e.g., gears, belts, etc.).

Additional motion of the sensor 106 relative to the container 102 may be provided by the stage 104. For example, the stage 104 may be rotatable about the direction of the z-axis, indicated by shaft 612 and arrow 614. The stage 104 may also be translatable in the direction of the z-axis, as indicated by arrow 616. The rotation and translation provided by the stage 104 may be powered by a drive mechanism 628, which may also be under the control of the control device 110. The drive mechanism 628 may comprise one or more individual motors or other drive devices coupled to the stage 104 or shaft 612 to bring about rotation and translation. The drive device or devices may comprise one or more stepper motors, voice coil motors, hydraulic cylinders, pneumatic cylinders, etc.

Figure 7:
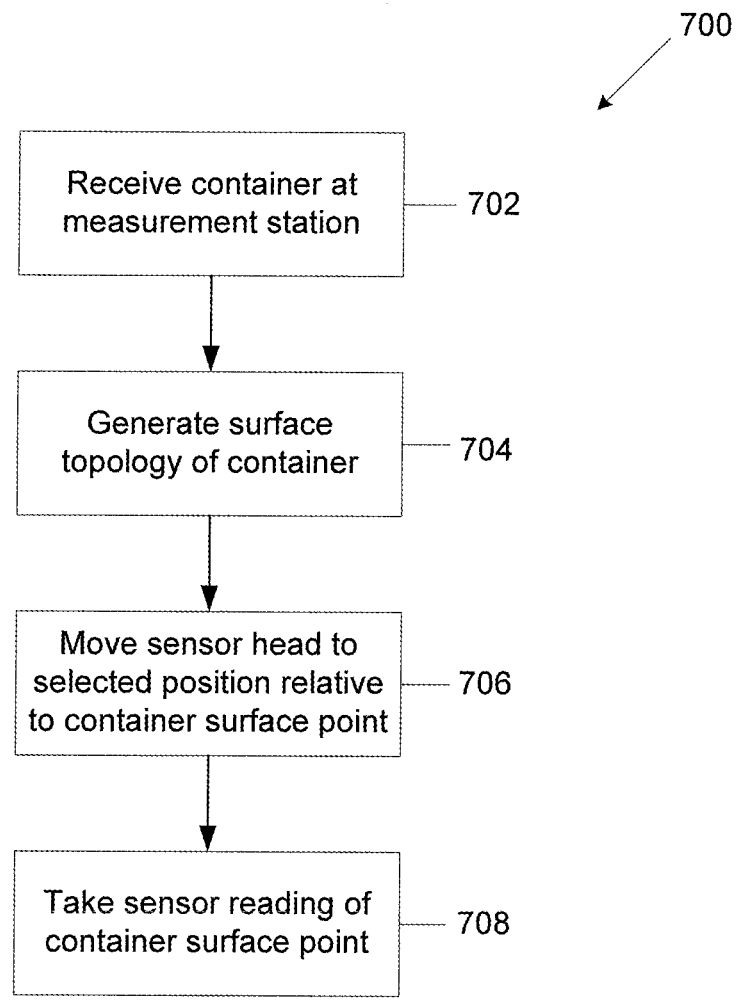
FIG. 7 illustrates one embodiment of a process flow using the system of FIG. 1 to measure properties of a container.

FIG. 7 illustrates one embodiment of a process flow 700 using the system 100 to measure properties of a container 102. At 702, the container 102 may be received at the measurement station (e.g., the stage 104). At 704, the control device 110 may generate a surface topology of the container 102. For example, this may involve creating a three dimensional approximation of the surface shape of the container 102. This may be created in various different manners. Several example methods of generating a surface topology of the container are described herein below. Also, in some embodiments, the surface topology of the container may be received from an outside source. For example, the shape and position of the container may be known. In some embodiments, the surface topology of the container 102 may be completely derived and/or received before thickness measurements commence. In other embodiments, however, the system may be configured to derive the surface topology of the container 102 bit-by-bit, for example, during the measurement process.

After having generated or received the surface topology, the control device 110 may be programmed to move the sensor 106 to a selected position relative to a first surface point on the container 102. For example, the control device 110 may direct the sensor positioning device 108 and/or the stage 104 to position the container 102 such that the sensor direction 112 is directed towards the first surface point. As described above, the normal distance from the sensor 106 to the first surface point may be a predetermined constant. Also, for example, the sensor direction 112 may be normal to the first surface point, for example, within a desired tolerance as described above. In placing the sensor 106 with the sensor positioning device 108, the control device 110 may utilize the surface topology described above. For example, the control device 110 may utilize the surface topology to find a position of the first surface point and a normal direction to the first surface point. This data may be utilized for placement of the sensor 106.

When the sensor 106 is positioned relative to the first surface point, the control device 110 may cause the sensor 106 to take a reading of the first surface point at 708. The reading may be any suitable type of reading capable of performance by the sensor 106. For example, the reading may indicate a distance of the container 102 from the sensor 106, a thickness of a wall of the container 102, a thickness of a coating on the container, etc.

According to various embodiments, the actions described at 706 and 708 may be repeated over multiple surface points of the container 102. The result may be a surface map of the container 102 showing properties (e.g., wall thickness, coating thickness, etc.) of multiple surface points. Results of the one or more measurements may be provided to a user in any suitable manner, for example, utilizing a user interface implemented on an output device such as, for example, a screen or printer. Also, in some embodiment, results of the one or more measurements may be provided in data form to a process control computer or other computer for processing.

Figure 8:
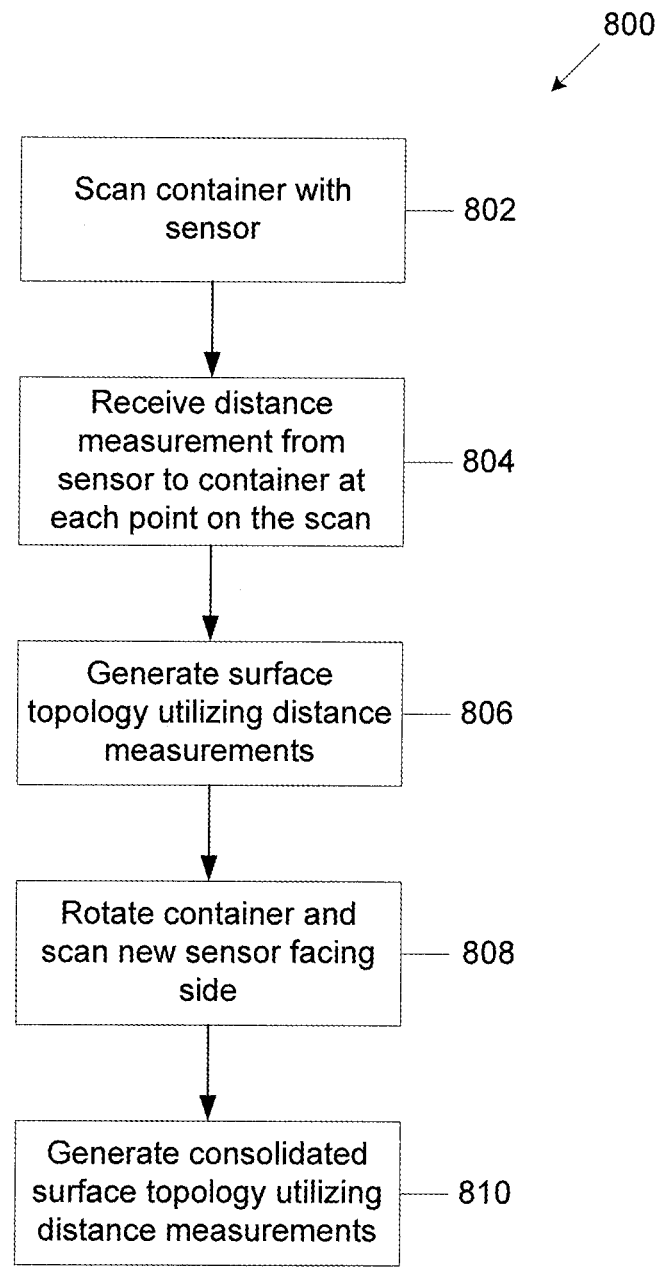
FIG. 8 illustrates one embodiment of a process flow for generating a surface topology of a container utilizing the system of FIG. 1.
Figure 9:
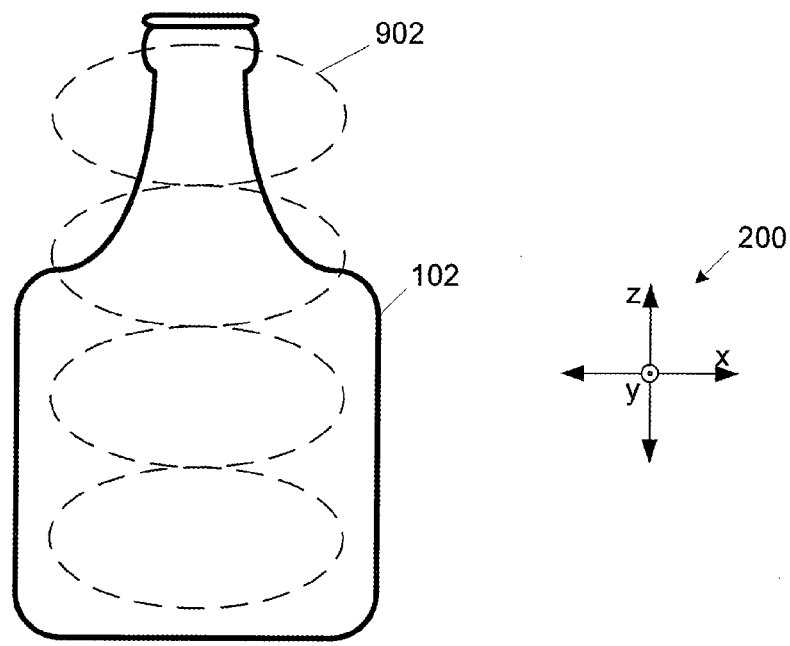
FIGS. 9 and 10 illustrate embodiments of the container showing example scan patterns.
Figure 10:
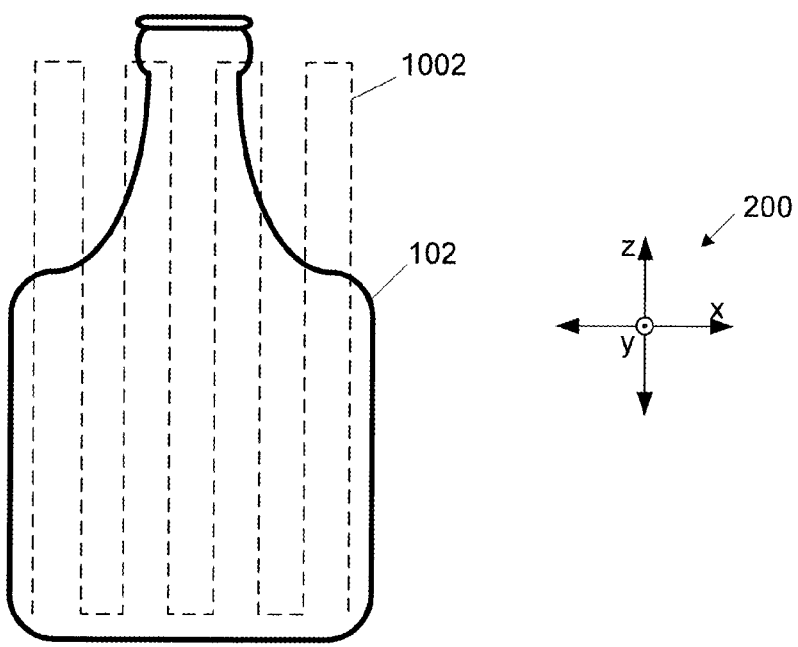

FIG. 8 illustrates one embodiment of a process flow 800 for generating a surface topology of a container 102 utilizing the system 100 described above. At 802, the control device 110 may cause the sensor positioning device 108 and/or the stage 104 to scan the container 102 with the sensor 106. FIGS. 9 and 10 illustrate embodiments of the container 102 showing example scan patterns. FIG. 9 illustrates a scan pattern 902 comprising a figure "8" pattern. FIG. 10 illustrates a scan pattern 1002 comprising a series of vertical and horizontal lines. The ratio of the length of the respective vertical and horizontal lines may vary depending on the application. During the scan, the sensor 106 may be confined to a defined plane, with the scanner 106 directed in a constant direction (e.g., perpendicular to the defined plane). For example, as illustrated in FIGS. 9 and 10, the defined plane may be parallel to the x-y plane.

Referring back to FIG. 8, at 804, the control device 110 may receive distance measurements from the sensor 106 at various points along the utilized scan pattern. For example, when the sensor 106 is configured to implement a chromatic measurement technique, as described above, the distance from the sensor 106 to the container 102 may be derived from the received signal. At 806, the control device 110 may generate a partial topology of the container 102 given the distance measurements received at 804. For example, the position of the sensor 106 at each of the readings may be known, and therefore cancelled from the distance readings, generating the partial topology. According to various embodiments, the partial topology may comprise only the points on the surface of the container 102 that were actually measured. In other embodiments, however, the control device 110 may extrapolate additional points from those that were measured. The extrapolation may be accomplished according to any suitable method including, for example, averaging, weighted averaging, etc. In some embodiments, the control device 110 may be programmed to extrapolate additional points of the surface topology of the container 102 by estimating the curvature between a set of two or more points where the position (e.g., distance from the sensor 106) is known. The topology may be partial because it may only include data showing the container 102 from one perspective.

At 808, the control device 110 may cause rotation of the container 102 relative to the sensor 106 and may repeat the actions of 802-806 with the new container orientation. The container 102 may be rotated by rotating the sensor 106 about a longitudinal axis of the container 102, rotating the stage 104 (and container 102), etc.

At 810, the control device 110 may consolidate partial topologies of the container 102 from different angles to generate a three dimensional topology of the container 102. This three-dimensional topology may then be used by the system 100 to take additional measurements requiring specific orientations of the sensor 106 relative to the container 102 (e.g., as described above with respect to process flow 700). The number of partial topologies combined to form the three-dimensional topology and, accordingly, the degree of rotation between partial topologies may be determined according to any suitable method. For example, in various embodiments, two partial topologies may be calculated with the container 102 rotated 180° between topologies. Also, in some embodiments, additional partial topologies taken at intermediate angles may be found and incorporated into the three dimensional topology. For example, in some embodiments, successive partial topologies may be separated by 1° or less. Methods utilizing relatively small angles between successive topologies may be well suited to measuring containers 102 having complex features.

Although the process flow 800 shows the generation of a complete topology, it will be appreciated that measuring properties of the container 102 may be measured based on partial topologies. For example, a partial topology of the container 102 may be found, as set forth at 806. Before rotating the container 102 relative to the sensor 106 at 808, the sensor 106 may be positioned relative to the surface of the container 102, as determined by the partial topology and/or previous partial topologies. For example, the sensor 106 may be positioned with the sensor direction 112 about normal to the surface and at the predetermined distance from the surface. When the sensor 106 is positioned, it may be used to measure a property of the container (e.g., thickness) at the surface position in the view of the sensor. After the portions of the container 102 described by the partial topology are measured, the container 102 may be rotated (808) and the next partial topology may be measured.

Figure 11:
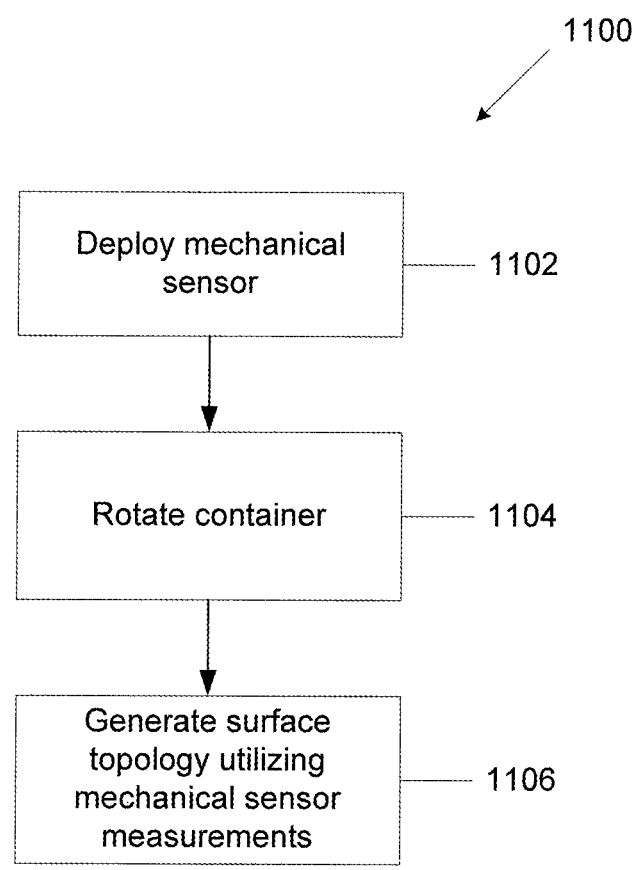
FIG. 11 illustrates another embodiment of a process flow for generating a surface topology of a container utilizing the system of FIG. 1.
Figure 12:
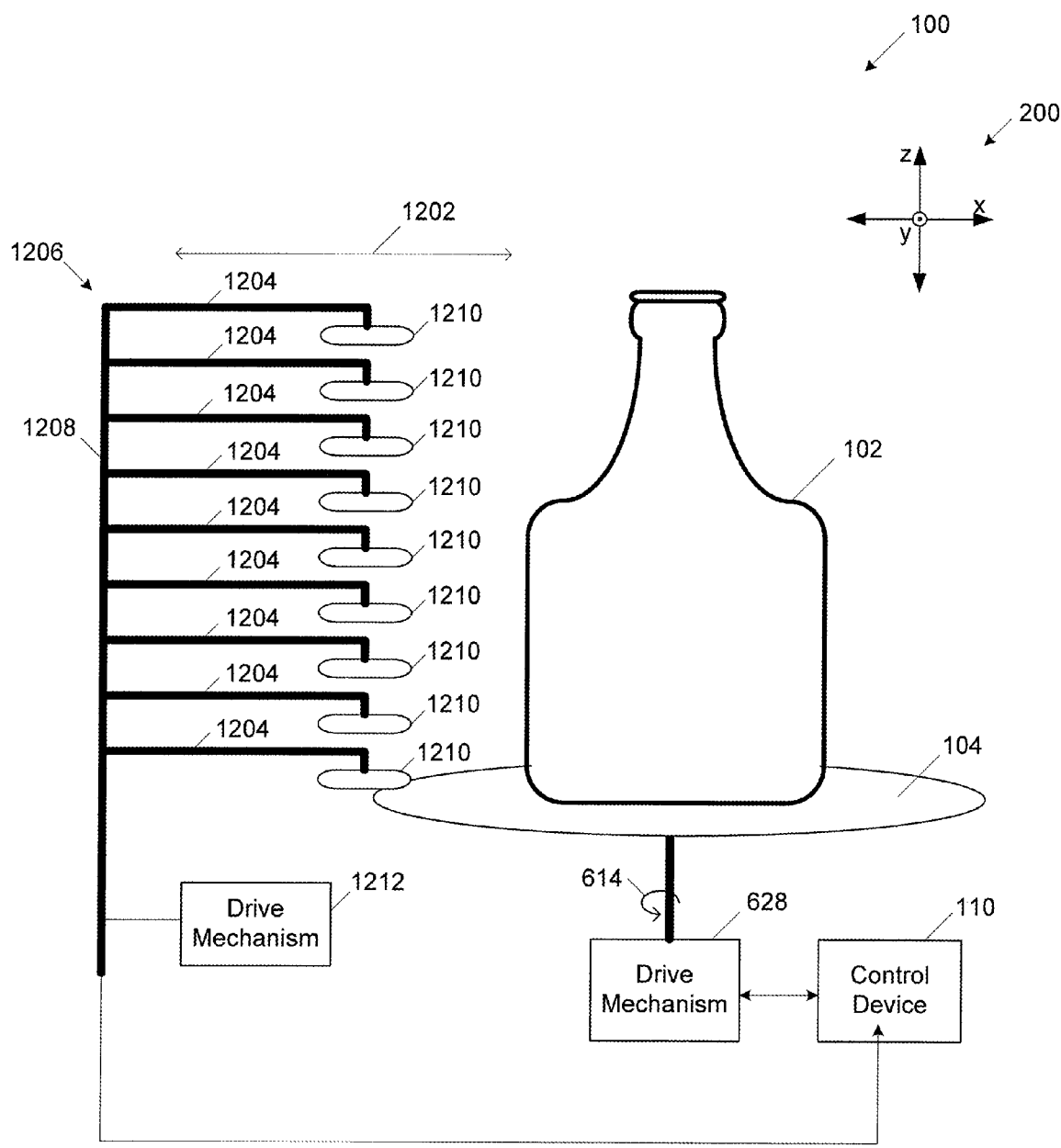
FIG. 12 illustrates one embodiment of the system of FIG. 1 comprising an example mechanical sensor.

FIG. 11 illustrates another embodiment of a process flow 1100 for generating a surface topology of a container. At 1102, a mechanical sensor may be deployed, for example, by the control device 110. FIG. 12 illustrates one embodiment of the system 100 comprising an example mechanical sensor 1206. The sensor 1206 shown in FIG. 12 comprises a member 1208 mechanically coupled to a plurality of deflectable arms 1204. Each of the deflectable arms 1204 may comprise a wheel 1210. In some embodiments, the wheels 1210 may be omitted. The mechanical sensor 1206 may be deployed by translating it toward the container 102 in the direction of the x-axis, indicated by arrow 1202. As the wheels 1210 contact the container 102, the respective arms 1204 may be deflected. The degree of deflection of each arm 1204 may be based on the shape of the container 102 at the position contacted by the wheel 1210. The mechanical sensor 1206 may additionally comprise sub-sensors at the interfaces between the member 1208 and each arm 1204 to generate a signal corresponding to the degree of deflection of each arm 1204. This data may be provided to the control device 110, resulting in a partial topology of the container 102. The sub-sensors may be any suitable type of sensor including, for example, mechanical sensors, strain gauges, etc. Translation of the sensor 1206 may be achieved when the control device 110 initiates operation of a drive mechanism 1212 coupled to the sensor 1206.

The drive mechanism may comprise any suitable stepper motor, voice coil motor, hydraulic cylinder, pneumatic cylinder, etc.

Referring back to FIG. 11, at 1104, the container 102 may be rotated with the sensor 1206 deployed. For example, the control device 110 may cause the drive mechanism 628 to rotate the stage 104, as indicated by arrow 614. Alternatively, the sensor 1206 may be rotated about the container. As the container 102 is rotated relative to the sensor 1206, the wheels 1210 may ride across surface features of the container 102, causing the arms 1204 to deflect in a manner corresponding to the surface features. In this way, the sub-sensors (not shown) may generate signals indicative of the surface topology of the container. At 1106, the control device 110 may utilize these signals to generate a surface topology of the container 102 that may be used, for example, as described above with respect to the flow chart 700.

Figure 13:
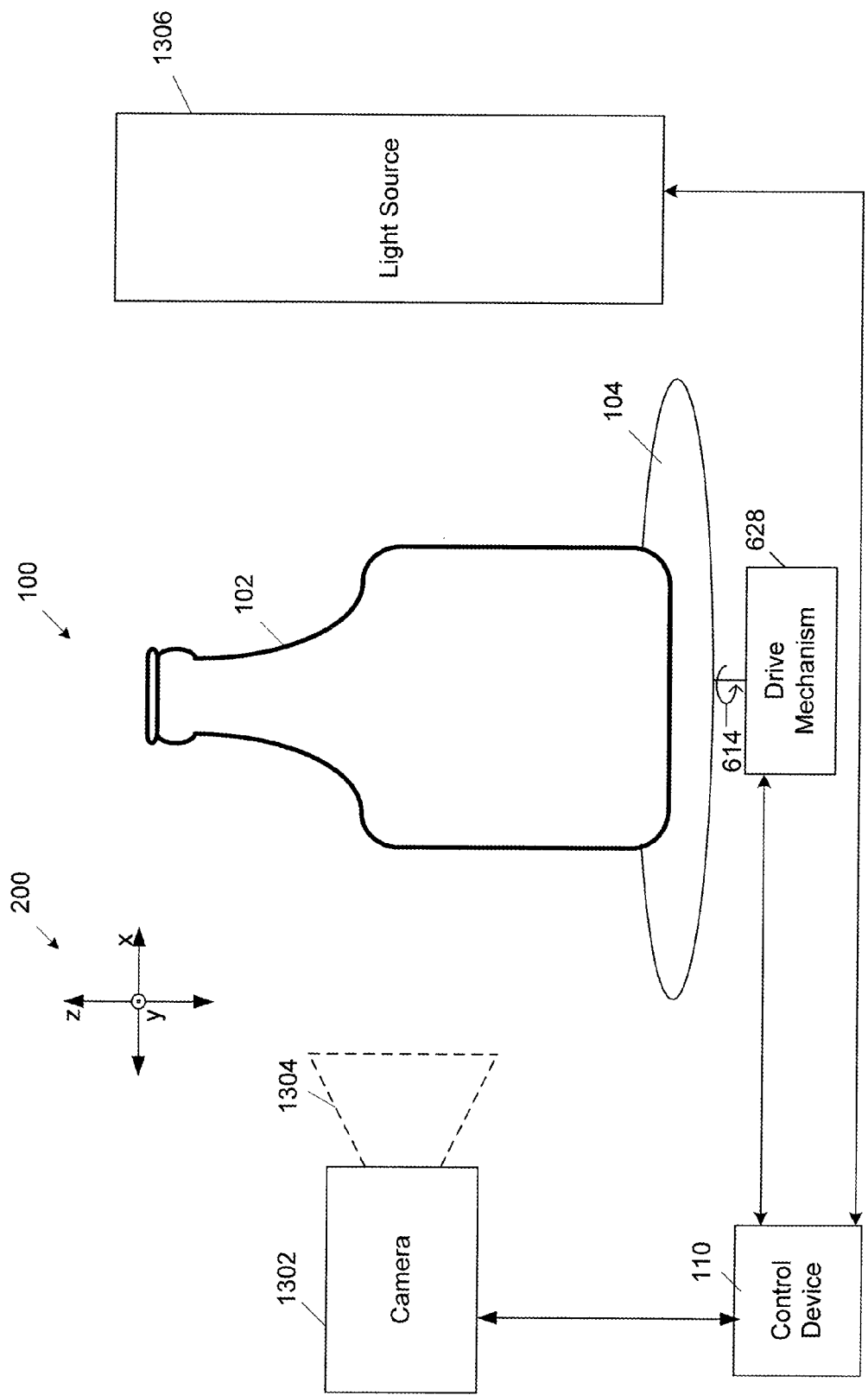
FIG. 13 illustrates another embodiment of the system of FIG. 1 comprising vision components for generating a surface topology of the container.

FIG. 13 illustrates another embodiment of the system 100 comprising vision components for generating a surface topology of the container 102. A camera 1302 may have a field of view 1304 which, at least when the camera 1302 is deployed, may include all or a portion of the container 102. The camera 1302 may be any suitable form of camera and, in some embodiments, may comprise a charge coupled device (CCD) with suitable optics. A light source 1306 may be positioned opposite the container 102 from the camera 1302, as shown, or at another suitable position or positions around the container 102. Images from the camera 1302 may be used, with or without readings from other sensors, to generate a surface topology of the container 102.

Figure 14:
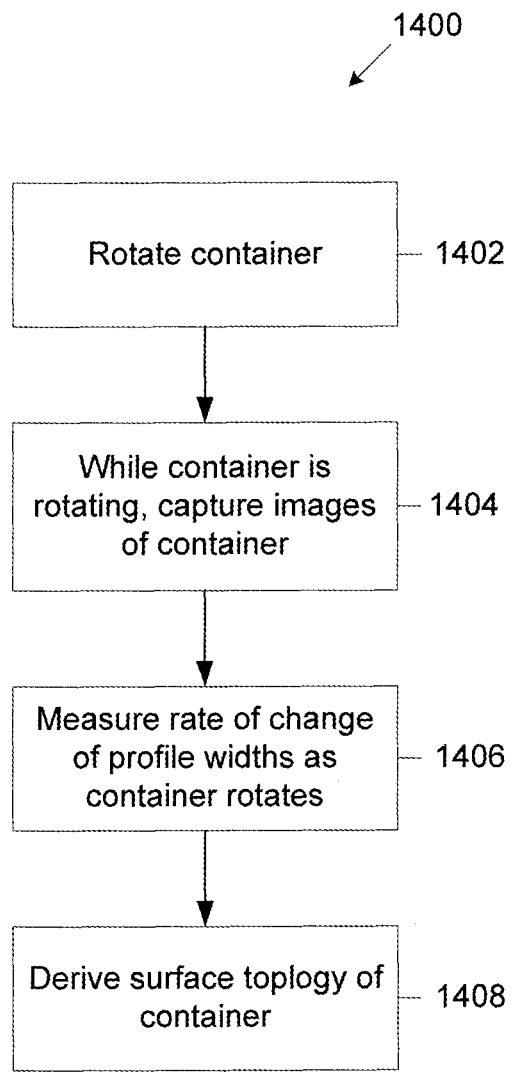
FIG. 14 illustrates one embodiment of a process flow for generating a surface topology of the container utilizing the vision components shown in FIG. 13.
Figure 15:
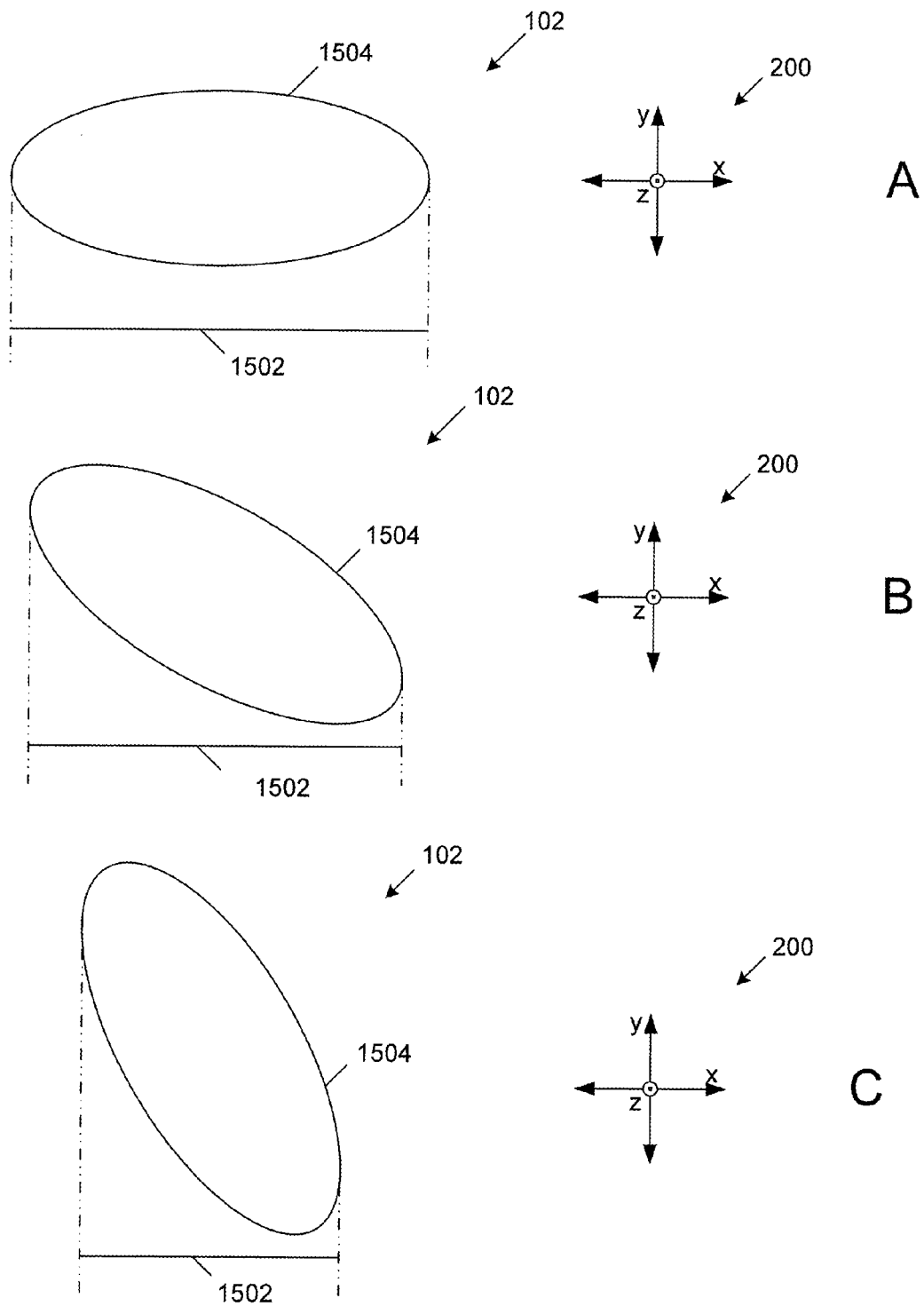
FIGS. 15A-15C illustrate an example container section at different stages of rotation.

FIG. 14 illustrates one embodiment of a process flow 1400 for generating a surface topology of the container 102 utilizing the vision components shown in FIG. 13. At 1402, the container 102 may be rotated. For example, the control device 110 may cause the drive mechanism 628 to rotate the stage 104 in the direction of the arrow 614, causing corresponding rotation of the container 102. At 1404, while the container 102 is rotating, the camera 1302 may capture a series of images of the container 102. Each of the images may include information describing a profile of the container 102 including, for example, measurable profile widths along the height of the container 102. For portions of the containers 102 that do not have a circular cross-section, the profile widths will change as the bottle rotates. For example, FIGS. 15A-15C illustrate an example container section 1504 at different stages of rotation. Each of the FIGS. 15A-15C illustrate a profile width 1502 visible to the camera 1302 at the illustrated orientations. It can be seen that, as the container 102 rotates, the profile width 1502 of the container section 1504 shrinks and grows. Referring back to FIG. 14, at 1406, the control device 110 may measure the direction and rate of change of the profile widths at different heights on the container as it rotates. This data may be combined with the profile widths themselves to generate a surface topology of the container 102 at 1408. In some embodiments, methods similar to the process flow 1400 may be particularly suited to containers 102 having convex cross-sections.

Figure 16:
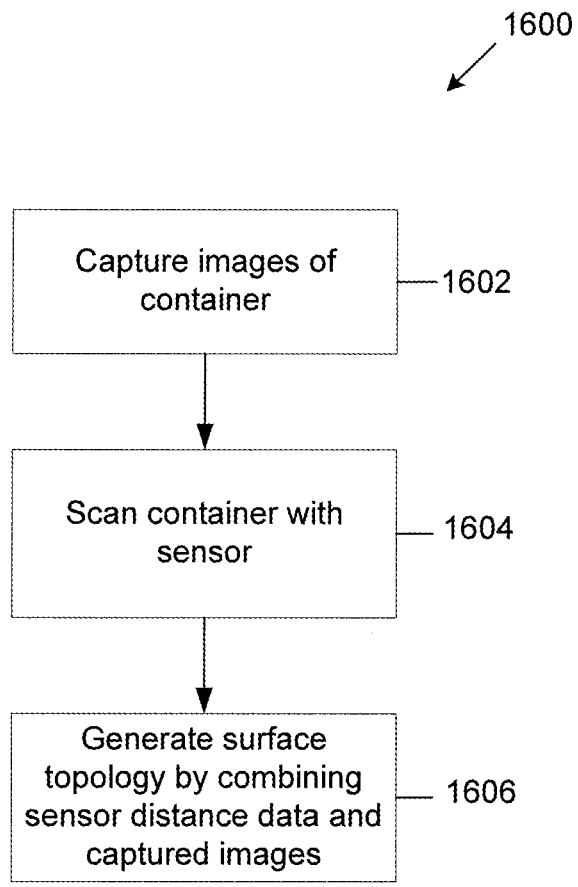
FIG. 16 illustrates one embodiment of a process flow for generating a surface topology of the container utilizing the sensor shown in FIG. 1 and the vision components shown in FIG. 13.

FIG. 16 illustrates one embodiment of a process flow 1600 for generating a surface topology of the container 102 utilizing the sensor 106 and the vision components shown in FIG. 13. At 1602, the control device 110 may cause the camera 1302 to capture one or more images of the container 102. These images, for example, may be captured either with the stage 104 stationary or rotating, as described above. At 1604, the control device 110 may cause the sensor control device 108 to scan the container 102 with the sensor 106, for example, as described herein above. Data resulting from the images and the scan may be combined to form a surface topology of the container 102. Use of a mixed method according to the process flow 1600 may reduce the rigor of measurements necessary to generate the complete surface topology. For example, it may not be necessary to scan the container 102 with the sensor 106 from as many angles if the data is to be combined with image data.

Figure 17:
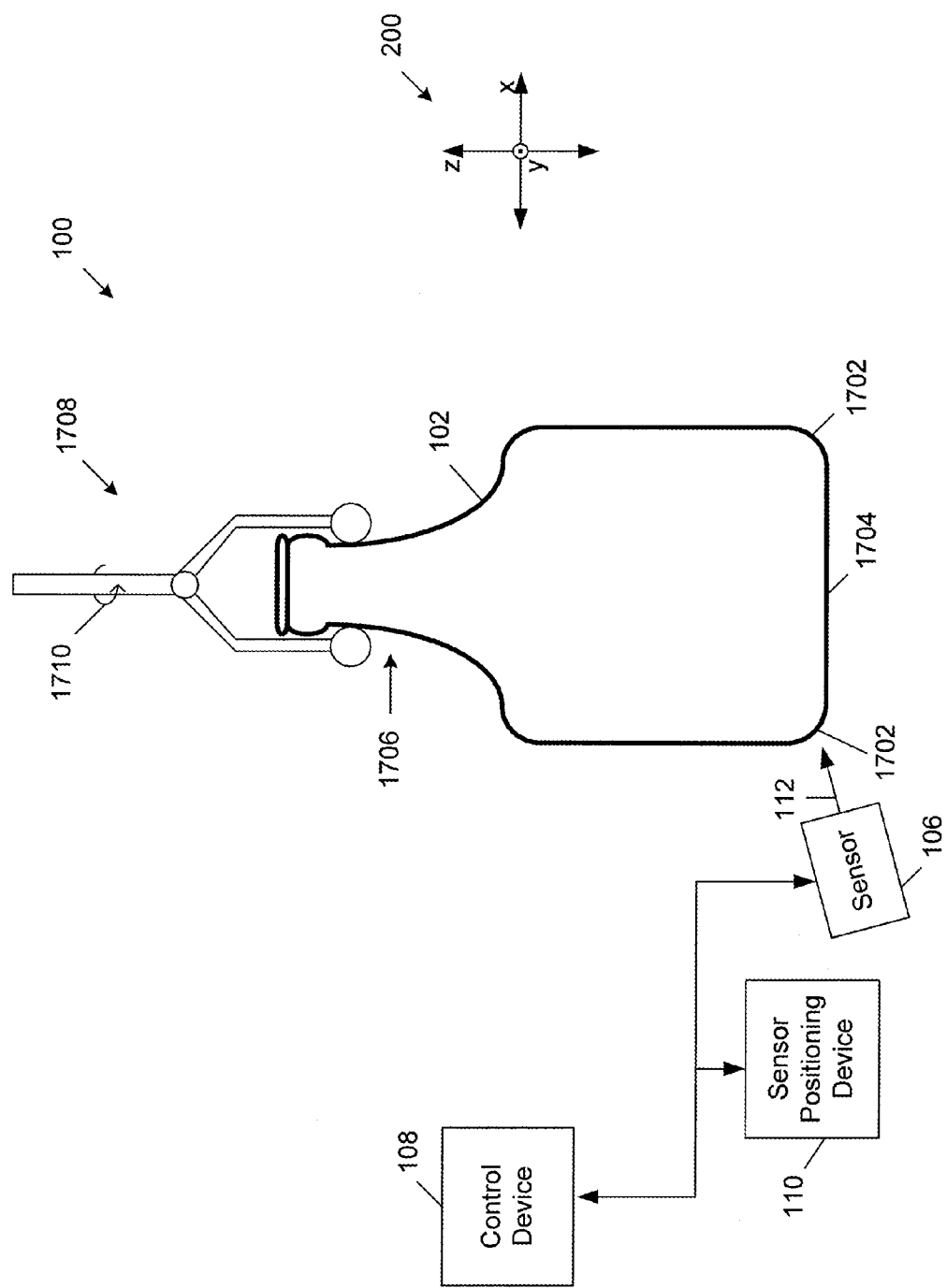
FIG. 17 illustrates one embodiment of the system of FIG. 1 configured for measuring a base and/or heel section of a container.

FIG. 17 illustrates one embodiment of the system 100 configured for measuring a base and/or heel section of a container. In FIG. 17, the base section of the container 102 is indicated by 1704 and heel sections are indicated by 1702. As illustrated, the stage 104 may be omitted to allow the sensor 106 to access the base 1704 and heel 1702 regions that may be obscured by the stage 104 when present. For example, the stage 104 may not be present at all. Also, for example, the container 102 and/or the stage 104 may be moved such that the stage 104 is not present. The container 102 may be suspended from any suitable device that does not overly obscure the base 1704 and heel 1702 regions. For example, in FIG. 17, the container is suspended by its neck 1706 from a mechanical arm 1708. The sensor 106, sensor positioning device 108 and control device 108 may operate as described herein above. For example, the sensor 106, or any other suitable sensor, may be utilized to derive a topology of the base 1704 and heel 1702 regions. The sensor positioning system 108 may position the sensor 106 about normal to a region of the base 1704 and/or heel 1702 regions to be measured and a reading may be taken. Rotation of the sensor 106 about the container 102 may be provided by the mechanical arm 1708, indicated by arrow 1710. In some embodiments, the sensor positioning device 108 may be configured to rotate the sensor 106 about the container 102.

It is to be understood that the figures and descriptions of the present invention have been simplified to illustrate elements that are relevant for a clear understanding of the present invention, while eliminating other elements, for purposes of clarity. Those of ordinary skill in the art will recognize that these and other elements may be desirable. However, because such elements are well known in the art and because they do not facilitate a better understanding of the present invention, a discussion of such elements is not provided herein.

In general, it will be apparent to one of ordinary skill in the art that at least some of the embodiments described herein, such as those including the control device 110, may be implemented utilizing many different embodiments of software, firmware, and/or hardware. The software and firmware code may be executed by a computer or computing device comprising a processor (e.g., a DSP or any other similar processing circuit). The processor may be in communication with memory or another computer readable medium comprising the software code. The software code or specialized control hardware that may be used to implement embodiments is not limiting. For example, embodiments described herein may be implemented in computer software using any suitable computer software language type, using, for example, conventional or object-oriented techniques. Such software may be stored on any type of suitable computer-readable medium or media, such as, for example, a magnetic or optical storage medium. According to various embodiments, the software may be firmware stored at an EEPROM and/or other non-volatile memory associated with a DSP or other similar processing circuit. The operation and behavior of the embodiments may be described without specific reference to specific software code or specialized hardware components. The absence of such specific references is feasible, because it is clearly understood that artisans of ordinary skill would be able to design software and control hardware to implement the embodiments based on the present description with no more than reasonable effort and without undue experimentation.

In various embodiments disclosed herein, a single component may be replaced by multiple components and multiple components may be replaced by a single component to perform a given function or functions. Except where such substitution would not be operative, such substitution is within the intended scope of the embodiments.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

We claim:

1. A system for measuring a thickness of a container defined by a height parallel to a z-axis direction, a width parallel to an x-axis direction, and a depth parallel to a y-axis direction, the system comprising:
    a chromatic thickness sensor, wherein the chromatic thickness sensor is configured to provide chromatically separated illumination to the container and to receive a reflection of the illumination from the container, wherein the illumination is directed to the container along a sensor direction;
    a multi-axis positioning system mechanically coupled to the sensor, wherein the multi-axis positioning system is positioned relative to the container to translate the sensor along the x-axis direction, to rotate the sensor about the z-axis direction and to rotate the sensor about the y-axis direction; and
    a control device comprising at least one processor and operatively associated data storage, wherein the data storage comprises instructions that, when executed by the at least one processor, cause the control device to:
    based on a surface topology of the container, generate a first instruction to the multi-axis positioning system to position the sensor relative to a first point on a surface of a container such that: a distance from the sensor to the first point is about equal to a first distance; and the sensor direction is about normal to the surface at the first point;
    receive a reading from the sensor indicating a thickness of the container at the first point;
    based on the surface topology of the container, generate a second instruction to the multi-axis positioning system to position the sensor relative to a second point on the surface of the container such that: a distance from the sensor to the second point is about equal to the first distance; and the sensor direction is about normal to the surface at the second point; and
    receive a reading from the sensor indicating a thickness of the container at the second point.

2. The system of claim 1, wherein the positioning system comprises a yoke coupled to the sensor wherein the sensor is pivotable relative to the yoke about a first axis.

3. The system of claim 2, wherein the yoke is pivotable relative to the container about a second axis parallel to the z-axis and about perpendicular to the first axis.

4. The system of claim 3, wherein the yoke is translable towards and away from the container along a first direction, wherein the first direction is about perpendicular to the first axis and the second axis.

5. The system of claim 1, wherein the data storage further comprises instructions that, when executed by the at least one processor, cause the control device to generate the surface topology.

6. The system of claim 5, wherein generating the surface topology comprises:
    instructing the positioning system to scan the sensor in a first plane relative to the container with the sensor direction about perpendicular to the first plane, with the container held substantially stationary during the scan; and
    with the sensor positioned at a plurality of sensor positions during the scan, receiving from the sensor data indicating a distance between the sensor and the surface of the container.

7. The system of claim 6, wherein generating the surface topology further comprises:
    instructing a stage to rotate the container by a first increment;
    instructing the positioning system to, after the container is rotated by the first increment, scan the sensor in the first plane relative to the container with the sensor direction about perpendicular to the first plane; and
    with the sensor positioned at a second plurality of sensor positions during the scan, receiving from the sensor second data indicating a distance between the sensor and the surface of the container.

8. The system of claim 6, wherein the increment is at least one of 180° and 1°.

9. The system of claim 5, wherein the system further comprises a mechanical topology sensor, the mechanical topology sensor comprising:
    a first sensor member;
    a plurality of deflectable arms coupled to the first sensor member and directed about perpendicular to the first sensor member; and
    a plurality of wheels coupled to the deflectable arms; and
    wherein generating the surface topology comprises:
    instructing a drive mechanism to deploy the mechanical topology sensor such that the plurality of wheels are in contact with the container;
    instructing a stage to rotate the container; and
    receiving from the mechanical topology sensor data describing a deflection of each of the plurality of deflectable arms as the container rotates.

10. The system of claim 5, wherein the system further comprises a camera in communication with the control device, and wherein generating the surface topology comprises capturing at least one image of the container with the camera.

11. The system of claim 10, wherein generating the surface topology further comprises:
    instructing a stage to rotate the container; and
    capturing a plurality of images of the container as it rotates.

12. The system of claim 11, wherein generating the surface topology further comprises:

extracting from each of the plurality of images a first profile diameter of the container at a first container height;
extrapolate from the plurality of images a direction and rate of change of the first profile diameter as the container rotates.

13. A method for measuring a thickness of a container defined by a height parallel to a z-axis direction, a width parallel to an x-axis direction, and a depth parallel to a y-axis direction, the method comprising:
based on a surface topology of the container, generating, by a control device, a first instruction to a multi-axis positioning system to position a chromatic thickness sensor relative to a first point on a surface of the container such that: a distance from the chromatic thickness sensor to the first point is about equal to a predetermined distance; and a sensor direction is about normal to the surface at the first point, wherein the sensor is configured to direct chromatically separated illumination towards the container and receive a reflection of the chromatically separated illumination from the container, and wherein the illumination is directed to the surface of the container along the sensor direction, wherein the control device comprises at least one processor and operatively associated memory;
receiving from the sensor data indicating a thickness of the container at the first point;
based on the surface topology of the container, generating, by the control device, a second instruction to the multi-axis positioning system to position the sensor relative to a second point of the container such that: a distance from the sensor to the surface at the second point is about equal to the predetermined distance; and the sensor direction is about normal to the surface at the second point, wherein the second instruction instructs the multi-axis position system to apply to the sensor at least one motion selected from the group consisting of translation along the x-axis direction, rotation about the z-axis direction and rotation about the y-axis direction; and
receive from the sensor data indicating a thickness of the container at the second point of the container.

14. The method of claim 13, further comprising generating the surface topology of the container considering received data indicating the surface topology of the container.

15. The method of claim 14, wherein generating the surface topology comprises:
instructing the positioning system to scan the sensor in a first plane relative to the container with the sensor direction about perpendicular to the first plane, with the container held substantially stationary during the scan; and
with the sensor positioned at a plurality of sensor positions during the scan, receiving from the sensor data indicating a distance between the sensor and the surface of the container.

16. The method of claim 15, wherein generating the surface topology further comprises:
instructing a stage to rotate the container by a first increment;
instructing the positioning system to, after the container is rotated by the first increment, scan the sensor in the first plane relative to the container with the sensor direction about perpendicular to the first plane; and
with the sensor positioned at a second plurality of sensor positions during the scan, receiving from the sensor second data indicating a distance between the sensor and the surface of the container.

17. The method of claim 15, wherein the increment is at least one of 180° and 1°.

18. The method of claim 14, wherein generating the surface topology comprises:
instructing a drive mechanism to deploy a mechanical topology sensor such that a plurality of wheels of the mechanical topology sensor are in contact with the container, wherein the mechanical topology sensor comprises:
a first sensor member;
a plurality of deflectable arms coupled to the first sensor member and directed about perpendicular to the first sensor member; and
the plurality of wheels coupled to the deflectable arms; and
instructing a stage to rotate the container; and
receiving from the mechanical topology sensor data describing a deflection of each of the plurality of deflectable arms as the container rotates.

19. The method of claim 14, wherein generating the surface topology comprises capturing at least one image of the container with a camera.

20. The method of claim 19, wherein generating the surface topology further comprises:
instructing a stage to rotate the container; and
capturing a plurality of images of the container as it rotates.

21. The method of claim 20, wherein generating the surface topology further comprises:
extracting from each of the plurality of images a first profile diameter of the container at a first container height;
extrapolate from the plurality of images a direction and rate of change of the first profile diameter as the container rotates.

* * * * *